US00PP31094P2

(12) United States Plant Patent
Westhoff

(10) Patent No.: US PP31,094 P2
(45) Date of Patent: Nov. 19, 2019

(54) ***PETUNIA* PLANT NAMED 'WESPECRATITO'**

(50) Latin Name: ***Petunia* x *hybrida***
Varietal Denomination: Wespecratito

(71) Applicant: Heinrich Westhoff, Sudlohn (DE)

(72) Inventor: Heinrich Westhoff, Sudlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 15/999,959

(22) Filed: Sep. 4, 2018

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.13
CPC ..... A01H 6/824; A01H 6/82; A01H 6/1424; A01H 6/42
See application file for complete search history.

*Primary Examiner* — June Hwu
(74) *Attorney, Agent, or Firm* — C. A. Whealy

(57) ABSTRACT

A new and distinct cultivar of *Petunia* plant named 'Wespecratito', characterized by its semi-upright to semi-trailing and mounding plant habit; moderately vigorous growth habit; freely branching habit; freely flowering habit; long flowering period; medium-sized flowers that are pale orange and red purple in color with a greyed purple star-shaped pattern; and good garden performance.

2 Drawing Sheets

Botanical designation: *Petunia* x *hybrida*.
Cultivar denomination: 'WESPECRATITO'.

BACKGROUND OF THE INVENTION

The present invention relates to a new and distinct cultivar of *Petunia* plant, botanically known as *Petunia* x *hybrida* and hereinafter referred to by the name 'Wespecratito'.

The new *Petunia* plant is a product of a planned breeding program conducted by the Inventor in Südlohn, Germany. The objective of the breeding program is to create new mounding and freely-flowering *Petunia* plants with unique and attractive flower colors.

The new *Petunia* plant originated from a cross-pollination made by the Inventor during the summer of 2014 in Südlohn, Germany of a proprietary selection of *Petunia* x *hybrida* identified as code designation 14P382A, not patented, as the female, or seed, parent with a proprietary selection of *Petunia* x *hybrida* identified as code designation 14P230Z, not patented, as the male, or pollen, parent. The new *Petunia* plant was discovered and selected by the Inventor as a single flowering plant within the progeny of the stated cross-pollination in a controlled greenhouse environment in Südlohn, Germany in April, 2015.

Asexual reproduction of the new *Petunia* plant by terminal vegetative cuttings in a controlled greenhouse environment in Südlohn, Germany since August, 2015 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Wespecratito'. These characteristics in combination distinguish 'Wespecratito' as a new and distinct *Petunia* plant:

1. Semi-upright to semi-trailing and mounding plant habit.
2. Moderately vigorous growth habit.
3. Freely branching habit.
4. Freely flowering habit.
5. Long flowering period.
6. Medium-sized flowers that are pale orange and red purple in color with a greyed purple star-shaped pattern.
7. Good garden performance.

Plants of the new *Petunia* can be compared to plants of the female parent selection. Plants of the new *Petunia* differ primarily from plants of the female parent selection in the following characteristics:

1. Plants of the new *Petunia* are more compact than plants of the female parent selection.
2. Plants of the new *Petunia* and the female parent selection differ in flower color as flowers of plants of the new *Petunia* are pale orange and red purple in color with a greyed purple star-shaped pattern whereas flowers of plants of the female parent selection do not have a star-shaped pattern.

Plants of the new *Petunia* can be compared to plants of the male parent selection. Plants of the new *Petunia* differ primarily from plants of the male parent selection in the following characteristics:

1. Plants of the new *Petunia* are more mounding than and not as upright as plants of the male parent selection.
2. Plants of the new *Petunia* have smaller flowers than plants of the male parent selection.

Plants of the new *Petunia* can be compared to plants of the *Petunia* x *hybrida* 'Wespecrabobust', not patented. In side-by-side comparisons, plants of the new *Petunia* and 'Wespecrabobust' differ primarily in flower color as flowers of plants of the new *Petunia* are pale orange and red purple in color with a greyed purple star-shaped pattern whereas flowers of plants of 'Wespecrabobust' are greyed yellow with a dark purple star-shaped pattern. In addition, plants of the new *Petunia* are not as upright as plants of 'Wespecrabobust'.

Plants of the new *Petunia* can also be compared to plants of the *Petunia* x *hybrida* 'Wespeoutpici', not patented. In side-by-side comparisons, plants of the new *Petunia* and 'Wespeoutpici' differ primarily in the following characteristics:

1. Plants of the new *Petunia* are more compact than plants of 'Wespeoutpici'.
2. Plants of the new *Petunia* are not as freely flowering as plants of 'Wespeoutpici'.
3. Plants of the new *Petunia* flower have larger flowers than plants of 'Wespeoutpici'.
4. Plants of the new *Petunia* and 'Wespeoutpici' differ in flower color as flowers of plants of the new *Petunia* are pale orange and red purple in color with a greyed purple star-shaped pattern whereas flowers of plants of 'Wespeoutpici' are red purple and white in color and do not have a star-shaped pattern.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph in the first sheet comprises a side perspective view of a typical flowering plant of 'Wespecratito' grown in a container.

The photograph on the second sheet is a close-up view of a typical flowering plant of 'Wespecratito'.

DETAILED BOTANICAL DESCRIPTION

The aforementioned photographs and following observations, measurements and values describe plants grown in 12-cm containers in Südlohn, Germany, under typical commercial cultural practices during the late spring and summer in a glass-covered greenhouse with day temperatures ranging from 20° C. to 38° C., night temperatures ranging from 16° C. to 20° C. and light levels ranging from 3 to 50 klux. Plants were 18 weeks old when the photographs and description were taken. In the following description, color references are made to The Royal Horticultural Society Colour Chart, 2001 Edition, except where general terms of ordinary dictionary significance are used.

Botanical classification: *Petunia* x *hybrida* 'Wespecratito'.

Parentage:

*Female, or seed, parent*.—Proprietary selection of *Petunia* x *hybrida* identified as code designation 14P382A, not patented.

*Male, or pollen, parent*.—Proprietary selection of *Petunia* x *hybrida* identified as code designation 14P230Z, not patented.

Propagation:

*Type*.—By terminal vegetative cuttings.

*Time to initiate roots, summer*.—About 14 to 20 days at temperatures about 18° C. to 20° C.

*Time to initiate roots, winter*.—About 21 to 24 days at temperatures about 18° C. to 20° C.

*Time to produce a rooted young plant, summer*.—About three to four weeks at temperatures about 18° C. to 20° C.

*Time to produce a rooted young plant, winter*.—About four to five weeks at temperatures about 18° C. to 20° C.

*Root description*.—Medium in thickness, fibrous; close to 158A in color.

*Rooting habit*.—Freely branching; medium density to dense.

Plant description:

*Plant form and growth habit*.—Semi-spreading to semi-trailing and mounding plant habit; freely branching habit with about eight primary lateral branches developing per plant; pinching enhances lateral branch development; moderately vigorous growth habit.

*Plant height*.—About 17 cm.

*Plant diameter*.—About 33 cm.

Lateral branch description:

*Length*.—About 16 cm.

*Diameter*.—About 3 mm to 4 mm.

*Internode length*.—About 8 mm to 16 mm.

*Strength*.—Strong, flexible.

*Aspect*.—Mostly outwardly.

*Texture*.—Densely pubescent; viscid.

*Color*.—Close to 146B.

Leaf description:

*Quantity and arrangement*.—Alternate, simple; sessile.

*Length*.—About 4.7 cm.

*Width*.—About 2 cm.

*Shape*.—Lanceolate.

*Apex*.—Acute.

*Base*.—Attenuate.

*Margin*.—Entire.

*Texture and luster, upper and lower surfaces*.—Densely pubescent; viscid; matte.

*Venation pattern*.—Pinnate.

*Color*.—Developing and fully expanded leaves, upper surface: Close to 137A; venation, close to 137B. Developing and fully expanded leaves, lower surface: Close to 137C; venation, close to 137D.

Flower description:

*Flower arrangement and habit*.—Medium-sized single-type salverform flowers arising from upper leaf axils; freely flowering habit with usually about one or two flowers developing per lateral branch and numerous flowers developing per plant during the flowering season; flowers face mostly upright to outwardly.

*Fragrance*.—None detected.

*Natural flowering season*.—Long flowering period, flowering commences naturally during April and plants flower continuously throughout the summer until frost in Germany.

*Flower longevity*.—Individual flowers last about three to five days on the plant; flowers not persistent.

*Flower buds*.—Length: About 3.4 cm. Diameter: About 5 mm. Shape: Oblong. Color: Towards the base, close to 177D; mid-section, close to 177A and 144B; towards the apex, close to 187B and 144B.

*Flower diameter*.—About 5.3 cm.

*Flower height*.—About 4.5 cm.

*Flower throat diameter*.—About 1 cm.

*Flower tube length*.—About 2.6 cm.

*Flower tube diameter, proximally*.—About 4 mm.

*Corolla*.—Quantity and arrangement: Five in a single whorl, fused at the base and opening into a flared trumpet. Petal length from throat: About 2.4 cm. Petal width: About 2.7 cm. Petal shape: Roughly spatulate. Petal apex: Cuspidate. Petal margin: Entire; slightly undulate. Petal texture and luster, upper and lower surfaces: Smooth, glabrous; matte. Throat texture: Smooth, glabrous. Tube texture: Pubescent. Color: Petal, when opening, upper surface: Close to 31A and 54A; star-shaped pattern (petals' fusion), close to 59A. Petal, when opening, lower surface: Close to 145A to 145C and 72B. Petal, fully opened, upper surface: Close to N25C to N25D, 26D and 66A; star-shaped pattern (petals' fusion), close to 187A to 187C; venation, close to 14B; with development, color becoming closer to 79C and N155C and 16D. Petal, fully opened, lower surface: Close to 145C and 72B; venation, close to 144B; with development, color becoming closer to 77A to 77B and 145C to 145D with development. Throat: Close to 23A to 23B and N34A; venation, close to 14B. Tube: Close to 78A to 78B and 145C to 145D; venation, close to 144B.

*Calyx*.—Arrangement: One star-shaped calyx tube with five sepals arranged in a single whorl and fused at the base. Sepal length: About 1.4 cm. Sepal width: About 3 mm. Sepal shape: Oblong. Sepal apex: Acute. Sepal margin: Entire. Sepal texture and luster, upper and lower surfaces: Pubescent; matte. Color, upper and lower surfaces: Close to 146A.

*Peduncles*.—Length: About 1 cm. Diameter: About 1.5 mm. Strength: Strong, flexible. Aspect: Upright to outwardly. Texture: Pubescent. Color: Close to 144A to 144B.

*Reproductive organs*.—Stamens: Quantity per flower: Five. Filament length: About 9 mm to 11 mm. Filament color: Close to 155A. Anther shape: Four-parted, ovate. Anther size: About 2.3 mm by 2.5 mm. Anther color: Close to 160D. Pollen amount: Abundant. Pollen color: Close to 156C. Pistils: Quantity per flower: One. Pistil length: About 1.8 cm. Style length: About 1.8 cm. Style color: Close to 145A. Stigma shape: Ovate. Stigma color: Close to 146A to 146C. Ovary color: Close to 144B. Seeds and fruits: To date, seed and fruit development have not been observed on plants of the new *Petunia*.

Garden performance: Plants of the new *Petunia* have been observed to have good garden performance and to tolerate rain, wind and temperatures ranging from about 5° C. to about 38° C.

Pathogen & pest resistance: To date, plants of the new *Petunia* have not been observed to be resistant to pathogens and pests common to *Petunia* plants.

It is claimed:

1. A new and distinct *Petunia* plant named 'Wespecratito' as illustrated and described.

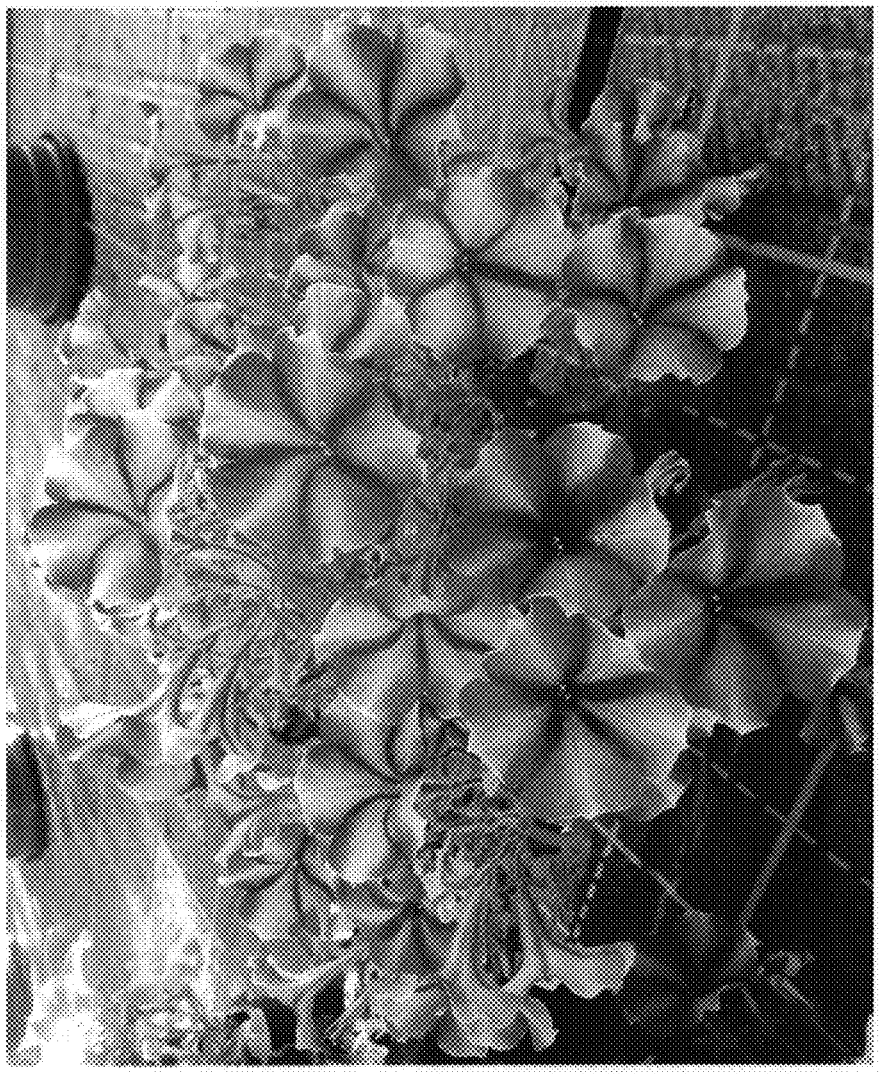

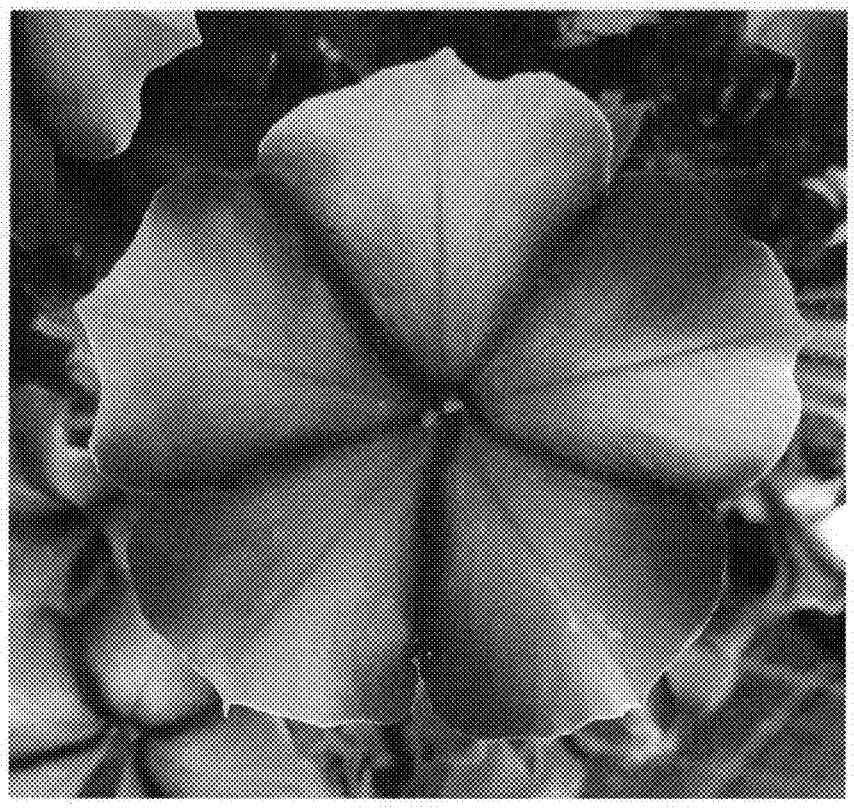

* * * * *